US011540248B2

(12) United States Patent
Scialò et al.

(10) Patent No.: US 11,540,248 B2
(45) Date of Patent: Dec. 27, 2022

(54) MOBILE MONITORING DEVICE FOR CONTROLLED CONTAMINATION AREAS

(71) Applicants: Particle Measuring Systems, Inc., Boulder, CO (US); Pharma Integration S.R.L., Siena (IT)

(72) Inventors: Giovanni Scialò, Frascati (IT); Davide Recchia, Frascati (IT); Claudio Bechini, Siena (IT)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 102 days.

(21) Appl. No.: 17/087,906

(22) Filed: Nov. 3, 2020

(65) Prior Publication Data
US 2021/0136722 A1  May 6, 2021

(30) Foreign Application Priority Data
Nov. 4, 2019  (IT) .......................... 102019000020248

(51) Int. Cl.
*H04W 64/00* (2009.01)
*H02J 7/00* (2006.01)

(52) U.S. Cl.
CPC ......... *H04W 64/006* (2013.01); *H02J 7/0048* (2020.01); *H04W 64/003* (2013.01)

(58) Field of Classification Search
CPC .. H04W 64/006; H04W 64/003; H04J 7/0048
See application file for complete search history.

(56) References Cited

U.S. PATENT DOCUMENTS

| 4,594,715 A | 6/1986 | Knollenberg |
| 4,798,465 A | 1/1989 | Knollenberg |
| 4,893,928 A | 1/1990 | Knollenberg |
| 5,282,151 A | 1/1994 | Knollenberg |

(Continued)

FOREIGN PATENT DOCUMENTS

DE   10346216 B3   9/2004

OTHER PUBLICATIONS

"Robotics Materials Handling: The Future is Closer than You Think," (2018) Modern Materials Handling, Peerless Content Creation, pp. 1-41.

(Continued)

*Primary Examiner* — Justin Y Lee
(74) *Attorney, Agent, or Firm* — Leydig, Voit & Mayer, Ltd.

(57) ABSTRACT

A mobile monitoring device for monitoring controlled contamination areas may include a motorized mobile structure, a sampling unit, and a central management and control unit. The motorized mobile structure is configured to move within an area to be monitored. The sampling unit is positioned on said mobile structure, and configured to perform sampling operations of air and/or surfaces of said area and obtain sampling data. The central management and control unit is operatively connected to the mobile structure and to said sampling unit. The mobile structure may be controlled by the central unit to reach predefined points of the area to be monitored. The sampling unit may be selectively activated and/or deactivated by said central unit in correspondence with said predefined starting points of said sampling operations.

22 Claims, 4 Drawing Sheets

(56) References Cited

U.S. PATENT DOCUMENTS

| | | |
|---|---|---|
| 5,283,199 A | 2/1994 | Bacon, Jr. et al. |
| 5,671,046 A | 9/1997 | Knowlton |
| 5,726,753 A | 3/1998 | Sandberg |
| 5,751,422 A | 5/1998 | Mitchell |
| 5,805,281 A | 9/1998 | Knowlton et al. |
| 5,861,950 A | 1/1999 | Knowlton |
| 5,889,589 A | 3/1999 | Sandberg |
| 5,903,338 A | 5/1999 | Mavliev et al. |
| 6,167,107 A | 12/2000 | Bates |
| 6,246,474 B1 | 6/2001 | Cerni et al. |
| 6,275,290 B1 | 8/2001 | Cerni et al. |
| 6,615,679 B1 | 9/2003 | Knollenberg et al. |
| 6,709,311 B2 | 3/2004 | Cerni |
| 6,859,277 B2 | 2/2005 | Wagner et al. |
| 6,903,818 B2 | 6/2005 | Cerni et al. |
| 6,928,892 B2 | 8/2005 | Storbeck et al. |
| 6,945,090 B2 | 9/2005 | Rodier |
| 7,030,980 B1 | 4/2006 | Sehler et al. |
| 7,088,446 B2 | 8/2006 | Cerni |
| 7,088,447 B1 | 8/2006 | Bates et al. |
| 7,208,123 B2 | 4/2007 | Knollenberg et al. |
| 7,235,214 B2 | 6/2007 | Rodier et al. |
| RE39,783 E | 8/2007 | Cerni et al. |
| 7,456,960 B2 | 11/2008 | Cerni et al. |
| 7,576,857 B2 | 8/2009 | Wagner |
| 7,667,839 B2 | 2/2010 | Bates |
| 7,746,469 B2 | 6/2010 | Shamir et al. |
| 7,796,255 B2 | 9/2010 | Miller |
| 7,916,293 B2 | 3/2011 | Mitchell et al. |
| 7,973,929 B2 | 7/2011 | Bates |
| 7,985,949 B2 | 7/2011 | Rodier |
| 8,027,035 B2 | 9/2011 | Mitchell et al. |
| 8,109,129 B2 | 2/2012 | Gorbunov |
| 8,154,724 B2 | 4/2012 | Mitchell et al. |
| 8,174,697 B2 | 5/2012 | Mitchell et al. |
| 8,427,642 B2 | 4/2013 | Mitchell et al. |
| 8,800,383 B2 | 8/2014 | Bates |
| 8,869,593 B2 | 10/2014 | Gorbunov et al. |
| 9,447,448 B1 | 9/2016 | Kozloski et al. |
| 9,592,609 B2 | 3/2017 | LaFary et al. |
| 9,631,222 B2 | 4/2017 | Ketcham et al. |
| 9,638,665 B2 | 5/2017 | Gorbunov |
| 9,682,345 B2 | 6/2017 | Gromala et al. |
| 9,808,760 B2 | 11/2017 | Gromala et al. |
| 9,810,558 B2 | 11/2017 | Bates et al. |
| 9,885,640 B2 | 2/2018 | Ketcham et al. |
| 9,989,462 B2 | 6/2018 | Lumpkin et al. |
| 10,197,487 B2 | 2/2019 | Knollenberg et al. |
| 10,345,200 B2 | 7/2019 | Scialo et al. |
| 10,371,620 B2 | 8/2019 | Knollenberg et al. |
| 10,792,694 B2 | 10/2020 | Gorbunov et al. |
| 10,859,487 B2 | 12/2020 | Knollenberg et al. |
| 10,908,059 B2 | 2/2021 | Knollenberg et al. |
| 10,921,229 B2 | 2/2021 | Shamir |
| 10,928,293 B2 | 2/2021 | Knollenberg et al. |
| 10,997,845 B2 | 5/2021 | MacLaughlin et al. |
| 11,181,455 B2 | 11/2021 | Bates et al. |
| 11,215,546 B2 | 1/2022 | MacLaughlin et al. |
| 11,231,345 B2 | 1/2022 | Scialo et al. |
| 11,237,095 B2 | 2/2022 | Rodier et al. |
| 11,250,684 B2 | 2/2022 | MacLaughlin et al. |
| 11,255,760 B2 | 2/2022 | Scialo et al. |
| 2005/0028593 A1 | 2/2005 | Rodier |
| 2006/0293794 A1* | 12/2006 | Harwig ............... G05D 1/0261 |
| | | 180/23 |
| 2009/0078862 A1 | 3/2009 | Rodier et al. |
| 2009/0190128 A1 | 7/2009 | Cerni et al. |
| 2009/0268202 A1 | 10/2009 | Wagner |
| 2012/0259481 A1* | 10/2012 | Kim ..................... G05D 1/0044 |
| | | 701/25 |
| 2015/0000595 A1 | 1/2015 | Gorbunov et al. |
| 2015/0059120 A1* | 3/2015 | Riehl ........................ A47L 9/06 |
| | | 15/340.3 |
| 2015/0259723 A1 | 9/2015 | Hartigan et al. |
| 2016/0126081 A1 | 5/2016 | Gorbunov |
| 2016/0139013 A1 | 5/2016 | Gorbunov |
| 2019/0250785 A1 | 8/2019 | Pandolfi et al. |
| 2019/0331701 A1 | 10/2019 | Polley et al. |
| 2020/0072729 A1 | 3/2020 | Lumpkin et al. |
| 2020/0150018 A1 | 5/2020 | Shamir |
| 2020/0240896 A1 | 7/2020 | Karasikov et al. |
| 2021/0044978 A1 | 2/2021 | Michaelis et al. |
| 2021/0063349 A1 | 3/2021 | Rodier et al. |
| 2021/0136722 A1 | 5/2021 | Scialo et al. |
| 2021/0140867 A1 | 5/2021 | Knollenberg et al. |
| 2021/0190659 A1 | 6/2021 | Knollenberg et al. |
| 2021/0208054 A1 | 7/2021 | Ellis et al. |
| 2021/0223273 A1 | 7/2021 | Scialo et al. |
| 2021/0381948 A1 | 12/2021 | Rodier et al. |
| 2021/0404936 A1 | 12/2021 | Bates et al. |

OTHER PUBLICATIONS

Schneider et al. (2012) "Unmanned multi-robot CBRNE reconnaissance with mobile manipulation—system description and technical validation," Proceedings of the 13th International Carpathian Control Conference (ICCC), pp. 637-642.

International Search Report and Written Opinion dated Feb. 5, 2021 in corresponding International Application No. PCT/US2020/058657, 12 pp.

* cited by examiner

MOBILE MONITORING DEVICE FOR CONTROLLED CONTAMINATION AREAS

CROSS-REFERENCE TO RELATED APPLICATIONS

This application claims the benefit of priority to Italian Patent Application No. 102019000020248, filed Nov. 4, 2019, which is hereby incorporated by reference in its entirety.

TECHNICAL FIELD OF INVENTION

This invention refers to a mobile monitoring device for areas with controlled contamination, in particular for clean rooms.

BACKGROUND OF INVENTION

The use of controlled contamination environments is widespread in many sectors, for example in pharmaceuticals, food and electronics, in order to ensure high quality standards.

Clean rooms, are environments in which the concentration and size of particles or micro-powders must be controlled and kept within limits dictated by specific ISO and sector standards. Each industry that involves the use of clean rooms, for example pharmaceuticals and micro-electronics, but also food and research laboratories, must comply with specific limits of concentration of particles and other contaminants such as bacteria, spores and pathogens in general.

Both the ISO standards and the industry standards provide for periodic checks of the clean rooms, with monitoring activities aimed at verifying compliance with the specified upper limits and, in general, with the standard conditions required. Monitoring operations usually involve the following steps:
  entry of tools and personnel into the clean room;
  positioning and tooling of the instruments in the points selected as samples;
  start of monitoring;
  moving to the next monitoring point;
  exit from the clean room.

The monitoring activities therefore require specialized personnel able to manually perform some delicate operations in the clean room to be monitored, for example transporting and assembling the equipment in the various parts of the room.

The presence of people during the monitoring is an inconvenience for various reasons. In fact, people represent a risk of contamination of the clean room; therefore limiting their presence leads to greater sterility.

Human intervention in monitoring activities represents a risk not only in terms of contamination, but also for the occurrence of false positives, with significant economic consequences.

In addition, human interventions involve factors of uncertainty about the work performed. In fact, manual operations do not guarantee repeatability of operations, which is necessary for a good construction of reliable data aimed at optimizing production and at the same time guaranteeing its quality.

Furthermore, a good sampling plan should include both data collected with environment at rest, with production plants stopped and in the absence of personnel, and sampling in operation. The presence of personnel during the sampling itself does not allow a good construction of the mapped data.

To all this, add that the staff must be trained and monitored for proper dressing, for entry into clean rooms and for the operation of sampling.

All this makes human interventions disadvantageous from both an economic and operational point of view.

SUMMARY OF THE INVENTION

The technical problem posed and solved by the present invention is therefore that of providing a mobile monitoring device for contaminated areas controlled which allows to overcome the drawbacks mentioned above with reference to the known art.

This problem is solved by a mobile monitoring device for controlled contamination areas according to claim 1. The invention also provides a system for monitoring areas a controlled contamination according to claim 12.

In one embodiment, a mobile monitoring device for monitoring controlled contamination areas comprises a motorized mobile structure, a sampling unit, and a central management and control unit. The motorized mobile structure is configured to move within an area to be monitored. The sampling unit is positioned on said mobile structure, and configured to perform sampling operations of air and/or surfaces of said area and obtain sampling data. The central management and control unit is operatively connected to the mobile structure and to said sampling unit. The mobile structure may be controlled by the central unit to reach predefined points of the area to be monitored. The sampling unit may be selectively activated and/or deactivated by said central unit in correspondence with said predefined starting points of said sampling operations.

In one embodiment, the device comprises a transceiver operatively connected to the central unit and configured to put the central unit in communication with one or more external peripheral devices via radiofrequency signals.

In one embodiment, the device comprises at least one memory unit operatively connected to at least one of the central unit and the sampling unit, configured to store the sampling data.

In one embodiment, the device comprises a navigation unit connected to the central unit, the configuration being such that the navigation unit transmits position data to the central unit with respect to which the device is guided in the predefined points.

In one embodiment, the navigation unit comprises at least one location unit configured to emit and/or receive position data comprising location information.

In one embodiment, the navigation unit comprises one or more navigation sensors located on the mobile structure and operatively connected to at least one of the central unit and the location unit, the navigation sensors being configured to detect position data including proximity information.

In one embodiment, the device comprises at least one radiofrequency detection sensor operatively connected to the central unit and configured to detect coded information and/or recordable data.

In one embodiment, the device comprises at least one robotic arm installed on the mobile structure, configured to interact with at least one sampling element usable in the sampling operations.

In one embodiment, the device comprises at least one digital camera configured for the acquisition of images and video, operatively connected to the central unit.

In one embodiment, the device comprises at least one interface unit operatively connected to at least the central unit and configured for interaction with a user.

In one embodiment, a monitoring system for monitoring controlled contamination areas comprises at least one mobile monitoring device, a data network, and an external peripheral device. The at least one mobile monitoring device comprises a motorized mobile structure, a sampling unit, and a central management and control unit. The motorized mobile structure is configured to move within an area to be monitored. The sampling unit is positioned on said mobile structure, and configured to perform sampling operations of air and/or surfaces of said area and obtain sampling data. The central management and control unit is operatively connected to the mobile structure and to said sampling unit. The mobile structure may be controlled by the central unit to reach predefined points of the area to be monitored. The sampling unit may be selectively activated and/or deactivated by said central unit in correspondence with said predefined starting points of said sampling operations. The data network is in operational communication with the at least one mobile monitoring device. The external peripheral device is operationally connected to the data network.

In one embodiment, the system comprises a plurality of reference units installed in the area to be monitored, each reference unit having a known position in a predefined reference system and configured to communicate with the device. In one embodiment, the reference units comprise RFID systems. In one embodiment, the reference units comprise GPS systems. In one embodiment, the reference units are configured to communicate with the central unit through the detection sensors via radio frequency transceivers. In one embodiment, the reference units are configured to communicate with the central unit via a digital camera of the device.

In one embodiment, the system comprises at least one charging station in operative communication with the device. In one embodiment, the device is configured such that when the quantity of energy of the device falls below a predefined level, the central unit directs the mobile structure to the charging station and couples the device to the charging station.

In one embodiment, the system comprises at least one sanitizing station operatively communicating with the device and configured to perform sanitizing and/or sterilization operations on said device.

In one embodiment, the system comprises at least one sanitizing station operatively communicating with the device and configured to perform sanitizing and/or sterilization operations on the device.

In one embodiment, the device is configured to navigate to predefined points of the area to be monitored and selectively activate the sampling unit at the predefined points.

Preferred features of the present invention are the subject of the dependent claims.

The present invention provides some relevant advantages. The main advantage consists in the fact that thanks to the device devised, human intervention can be remedied during the clean room monitoring phases.

The device devised, in fact, can be programmed to reach the sampling points within the clean room, start sampling and exit the clean room automatically, making human intervention unnecessary.

Other advantages are related to the operation of the device devised since, since the monitoring operations are automatic, the sampled values will be more reliable and more consistent with reality. Consequently, thanks to the device devised, it is possible to use the samples in qualitative production optimizations.

Other advantages, characteristics and methods of use of the present invention will become evident from the following detailed description of some embodiments, presented by way of non-limiting example.

BRIEF DESCRIPTION OF THE DRAWINGS

Reference will be made to the figures of the attached drawings, in which.

The thicknesses and curvatures shown in the figures introduced above are intended as purely illustrative, they are generally magnified and not necessarily shown in proportion.

DETAILED DESCRIPTION OF PREFERRED FORMS OF IMPLEMENTATION

Various embodiments and variants of the invention will be described below, and this with reference to the figures introduced above. Similar components are denoted in the various figures with the same numerical reference.

In the following detailed description, further embodiments and variants with respect to embodiments and variants already treated in the same description will be illustrated limitedly to the differences with what has already been disclosed. Furthermore, the different embodiments and variants described below are capable of being used in combination, where compatible.

Figure 1:
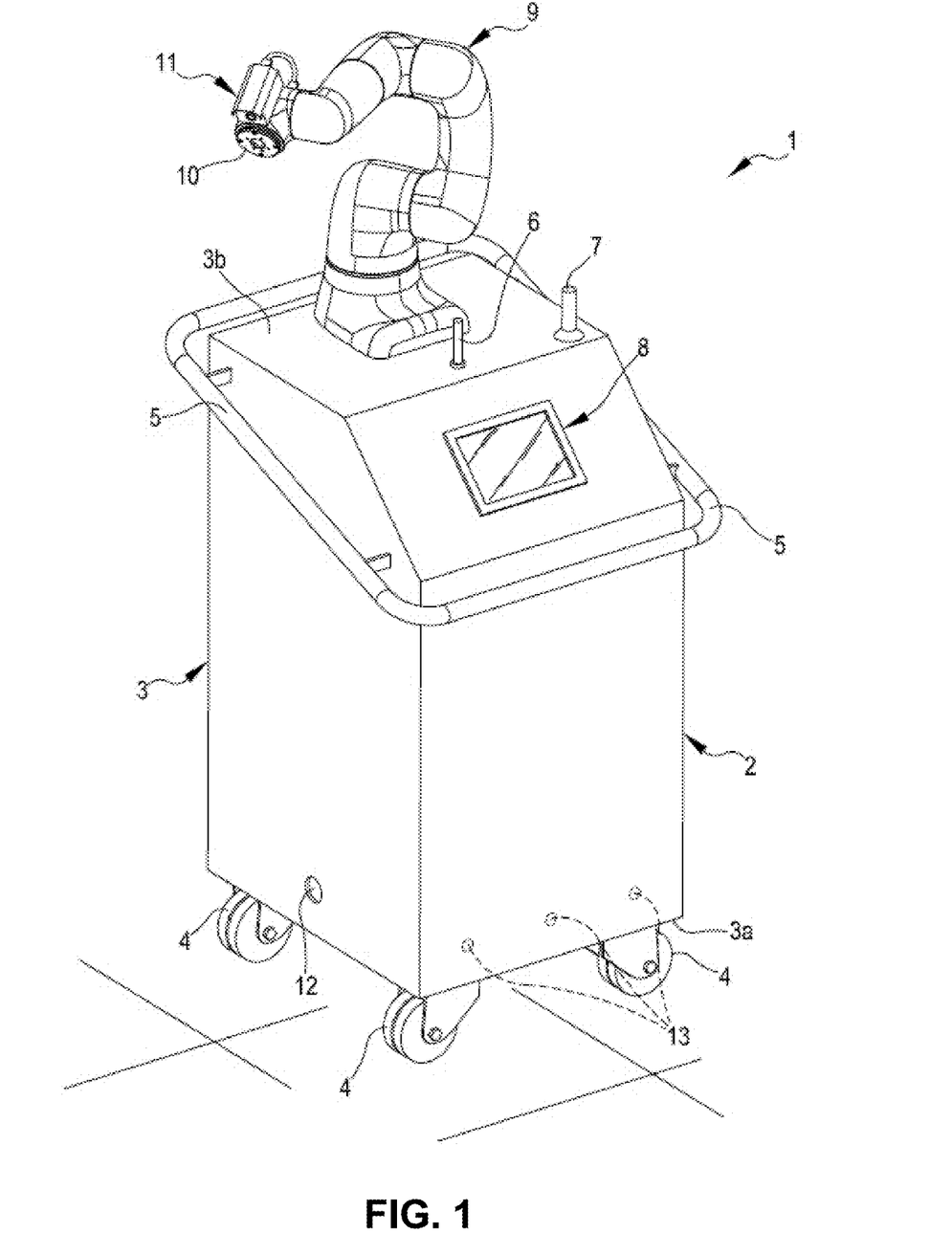
FIG. 1 shows a schematic perspective view of a preferred embodiment of the device according to the present invention.

With reference initially to FIG. 1, according to an embodiment of the invention, a mobile monitoring device for controlled contamination areas is generally denoted with 1. In this discussion, the terms "controlled contamination area" and "area to be monitored" are considered equivalent to the terms "clean room" or "clean room to monitor", respectively.

Device 1 includes a motorized mobile structure 2, configured to move within an area to be monitored. The mobile structure 2 includes wheels 4. The wheels 4 can be operated by electromotor means, for simplicity not shown in FIG. 1, selected from those available in the state of the art.

The mobile structure 2 can comprise a housing 3. Preferably the wheels are placed at the base 3a of the housing 3, but technically equivalent solutions are not excluded, for example in which the wheels 4 are arranged laterally to the housing 3.

The mobile structure 2 is usefully provided with a recharging socket 12, configured to be connected to an electric recharging station with which the device 1 can be supplied with energy. Optionally, the mobile structure 2 can be equipped with grip handles 5 configured to be gripped by a user, for example in order to push the mobile structure 2 to move it from one point to another.

Usefully, the mobile structure 2 can be provided with one or more openable compartments, not shown in FIG. 1, and configured to house sampling elements or other instrumentation useful for carrying out sampling operations.

The device 1 comprises a sampling unit positioned on the mobile structure 2, configured to carry out sampling operations suitable for obtaining sampling data. Sampling mainly concerns the air and surfaces present in the area to be monitored or clean room.

In particular, the sampling operations to be carried out can be those required by the reference technical standards, for example the ISO 14698-1/2 or ISO 14644-1/2/3 standards, or other industry standards. More specifically, the sampling operations can be one or more of the following:

air particle sampling;
microbiological sampling of the air;
sampling of environmental parameters such as relative humidity, temperature, absolute and/or differential pressures, the latter evaluated with respect to different rooms or rooms;
microbiological sampling of surfaces;
measurement of the speed with which air is introduced into the clean room;
Aerosol concentration measurement for filter integrity.

Advantageously, the sampling unit can comprise particle counter instruments, for example particle sensors known in the state of the art, for simplicity not shown in FIG. 1, and positioned at least partially inside the enclosure 3. The particle counter instruments are configured in such a way as to electronically count the particles present in the air passing through them.

For example, in one embodiment, the particle counter instruments may include a laser emitter configured to emit a laser beam through a flow of air passing through the instrument itself. The particle counter instruments may further comprise a detector configured to detect said laser beam emitted after passing through the flow of air. The configuration is such that, based on the effect of optical diffusion, or scattering, produced by the laser beam that strikes the particles, the counter instruments detect the number and size of the particles hit.

Particle counter instruments, therefore, can provide sampling data relating to the presence of particles, hereinafter referred to as "sampling data particles."

Furthermore, the sampling unit may include a duct 6, or commonly referred to as a "cone", through which the air coming from the clean room can be conveyed internally to the enclosure 3.

In particular, the duct 6 is associated with the particle counter instruments, the configuration being such that the air conveyed through the duct 6 is intercepted by the counter instruments and/or sensors and the particles present in it are retained and counted.

Conveniently, the duct 6 can have a configuration such as to compensate for the speed of the incoming air, keeping it constant.

Furthermore, the duct 6 can be suitably configured to maintain an isokinetic condition along its entire length, for example by suitably sizing the inlet section and the outlet section. To maintain constant flow with different inlet and outlet speeds, the cone may be designed with a ratio of the in and out areas such as to preserve isokinetic flow along its entire length.

Preferably, the sampling unit can comprise at least one microbiological sampler, also known as microbiological "impactor", for simplicity not shown in FIG. 1. The microbiological sampler can provide sampling data relating to the presence of bacteria and other microorganisms in the air, these data will be referred to below as "microbiological sampling data."

The device 1 can comprise a support 7 configured to engage one or more microbiological samplers. In particular, the microbiological sampler may be removably installed on the support 7 and can be replaced by other microbiological samplers to carry out subsequent sampling.

Usefully, each microbiological sampler may be provided with at least one Petri dish.

In use, the air can pass through the Petri dish installed on the support 7. Any microorganisms present in the air are retained by the Petri dish, with the microbiological sampler detecting information relating to retained microorganisms.

Usefully, the microbiological sampler can report air flow and volume data that can be used in subsequent analysis and in combination with information on retained microorganisms. Furthermore, the sampling unit may comprise one or more instruments to detect physical parameters of the air, taken individually or integrated with each other. For example, the sampling unit may include probes and/or sensors for detecting temperature, probes and/or sensors for detecting relative humidity, probes and/or sensors for detecting speed, as well as probes and/or sensors for detecting pressure and probes and/or sensors for detecting other physical environmental parameters.

The tools for detecting physical parameters can provide sampling data relating to the environmental parameters of the clean room, these data will hereinafter be referred to as "environmental sampling data".

Advantageously, the device 1 comprises a central management and control unit, or otherwise called CPU, operatively connected to the mobile structure 2 and to the sampling unit.

The configuration is such that the mobile structure 2 is controlled by the central unit to reach predefined points of the area to be monitored and the sampling unit is selectively activated/deactivated by the same central unit at the predefined points for the start of sampling operations.

In particular, the central unit is configured to control the mobile structure 2, activating/deactivating the start-up of the same structure, guiding it inside the clean room to reach predefined points where sampling operations may be started.

The central unit itself is configured to activate/deactivate the sampling unit, starting/ending air sampling operations. At the predefined points, the central unit activates the sampling unit for a preset time interval, allowing the acquisition of sampling data.

The central unit can selectively activate the sampling unit. For example, it can start one or more sampling operations for each predefined point, operating different samplings according to the type of acquisition requested, the type of clean room to be monitored and/or the specifications required by the applicable standards. Furthermore, the sampling operations may depend on the internal procedures for managing the clean room.

The choice of monitoring points, their position and their type of analysis derives from a preventive risk analysis, or risk analysis.

The central unit is usefully configured to receive input data useful for the calculation operations necessary for the operation of the central unit and, in general, of the device 1. The input data may include a topographic reference information related to the area to be monitored, parameters and reference values, identification information of predefined points or objects, values of time intervals and/or other parameters useful for carrying out the operations.

Preferably, the input data may already be contained in the central unit or they can be preset by a user.

Usefully, the central unit can include a machine learning unit configured to implement machine learning algorithms. Accordingly, the central unit can optimize sampling operations, suggesting and improving sampling strategies.

Advantageously, the device 1 can comprise one or more transceiver (for simplicity not shown in the figures) operationally connected to the central unit and configured to communicate the central unit with external peripheral devices using radio frequency signals.

Usefully, the transceivers are configured to communicate using radio frequency signals compatible with remote data transmission protocols, for example the Wi-Fi® protocol, Bluetooth® or other protocols.

This feature allows the central unit to receive and/or transmit data from remote external devices, for example outside the area to be monitored, as long as they are connected to a data network compatible with the protocols described above. The device 1 can therefore be connected to a data network and communicate and be operationally connected with peripheral devices connected to the same network. Among the peripheral devices it is useful to mention, by way of example, portable electronic devices such as smartphones and tablets, or fixed electronic devices, such as PCs or control stations.

A user, therefore, will be able to communicate remotely with the device 1 by means of peripheral devices, for example to set operational settings, or to check the progress of the work, or to guide the device along an established path.

Usefully, the device 1 comprises at least one memory unit, for simplicity not shown in FIG. 1, operationally connected to at least one of the central unit and the sampling unit, configured to store the sampling data.

The memory unit functions to store sampling data and other information. The data can be stored in memory and/or transmitted by via the transceiver(s) to the peripheral devices. In this way, by transmitting data to peripheral devices with greater memory capacity, it is possible to store a large amount of data. Furthermore, the link with external peripheral devices allows the real-time transmission of data and information to any operators responsible for supervising the monitoring operations.

By way of example, the stored sampling data may include:
- the values of environmental parameters such as temperature, pressure, speed, air, relative humidity and other required parameter values;
- information identifying the predefined point at which the sampling took place;
- time duration values of sampling operations.

Conveniently, the device 1 comprises a navigation unit connected to the central unit. The configuration is such that the navigation unit transmits position data to the central unit with respect to which the device is guided to the predefined points. In particular, the central unit processes the position data and on the basis thereof, sends commands to the mobile structure 2 to move the device to a predefined point.

In particular, the navigation unit can include at least one location unit configured to emit and/or receive location data including location information, hereinafter referred to as location data. According to a preferred embodiment, the location unit is placed inside the mobile structure 2, and is not visible in FIG. 1.

The location unit communicates the position of the device 1 with respect to a reference system, for example a known reference system, such as GPS, or a specially developed local system, and transmits data related to localization to the central unit.

Usefully, the central unit can include a topographic reference system containing topographic information of the area to be monitored in which device 1 is intended to move. By combining the position data with the topographic reference system, the central unit can calculate the path that the mobile structure 2 must travel to reach the predefined points to start sampling operations.

The reference system can be loaded directly into the central unit as a set of information, for example by means of interchange files known to the state of the art. Alternatively, the reference system can be provided to the central unit as a set of information provided by peripheral devices, for example, through two-way wireless transmission means.

Preferably, the navigation unit comprises one or more navigation sensors 13 placed on the mobile structure 2 and operationally connected to at least one of the central unit and the localization unit. The navigation sensors 13 are configured to detect position data including information of proximity. In particular, the navigation sensors can detect the presence of obstacles or other objects placed in the vicinity of the mobile structure 2. In this way the central unit can receive information on the presence of obstacles by modifying the path of the mobile structure 2 to avoid them.

In a preferred embodiment, illustrated in FIG. 1, the device 1 has navigation sensors 13 placed on the housing 3 in correspondence with the side wall facing the direction of advancement of the mobile structure 2. Conveniently, the navigation sensors can also be placed in other positions, for example on the back of the housing, or laterally to the housing 3 with respect to the direction of advancement.

By combining the position data, the central unit can calculate different paths and routes to reach the predefined points, managing to guide the mobile structure 2 within the area to be monitored and avoiding obstacles.

Advantageously, the device 1 can comprise at least one sensor of radio frequency detection operatively connected to the central unit and configured to detect coded information and/or recordable data. The sensor detection can be configured to use known radio frequency identification (RFID) technology or other similar technologies, for example known technology for reading bar codes.

The radio frequency detection sensor can identify the information coded by bar code, for example positioning points, tools or devices in the area to be monitored.

The radio frequency sensor can also record data on consumables for sampling, such as, for example, serial numbers, sampling duration, limit values, manufacturing date, expiration date, entered operator and other information relating to the consumable product and its use over time.

Optionally, the device 1 can also include at least one contact sensor, operatively connected to the central unit and configured to detect contact between the device and an obstacle. In case of contact, the sensor transmits related contact information to the central unit. The latter processes the information, orienting the mobile structure 2 accordingly.

Advantageously, the device 1 can comprise at least one robotic arm 9 installed on the mobile structure 2, configured to interact with at least one or more sampling elements that can be used in sampling operations.

In this discussion, the term "sampling element" refers to those elements, or devices, or tools, that can be used in sampling operations by means of specific positioning or extraction and archiving maneuvers. In one embodiment, swabs are used to take surface samples on instruments or devices present in clean rooms.

The swabs may be placed in contact with the surface to be sampled and, once the sampling is finished, they may be stored and stored for future laboratory analysis. In one embodiment, petri dishes may be placed on the support 7 and removed once the microbiological sampling has been carried out.

Thanks to the robotic arm 9, these operations, which were done manually by specialized operators, can now be done automatically.

In a preferred embodiment, the robotic arm 9 is installed on an upper wall 3b of the enclosure 3. The robotic arm 9 has an end terminal 10 configured to support an end device, referred to herein as an end effector. The terminal end 10 can support different types of end effectors, chosen according to the type of operations to be performed. In one embodiment of the sampling operations described above, an end effector configured to carry out gripping operations, for example having pliers or joints that reproduce the movements of a hand, may be employed. Different end effectors are also contemplated, for example those specially designed to pick up and store swabs, or to replace and place Petri dishes and/or impactors.

Usefully, the device 1 can comprise a digital camera 11 configured for the acquisition of images and videos, operationally connected to the central unit. The digital camera 11 allows transmission of live images of the monitoring operations, allowing an operator to remotely view, via the peripheral devices, the operations in progress. The digital camera 11 also allows recording images and videos of monitoring operations.

With reference to FIG. 1, the digital camera 11 can be positioned on the robotic arm 9, but different positions from the one illustrated are not excluded.

Advantageously, the device 1 comprises an interface unit operatively connected at least to the central unit and configured for interaction with a user. The interface unit is configured to provide the central unit with input data and other input information that can be used for the management and control of the device 1. For example, through the interface unit it is possible to enter the topographic information of the area to be monitored, or it is possible to select and program the operations to be carried out using an integrated software configured specifically.

A user can interact with the remote interface unit, through networked devices such as smartphones, tablets, fixed PCs or control stations.

Preferably, the interface unit can comprise a touchscreen 8 as shown in FIG. 1, allowing a user to interact directly with the device 1. Different solutions are not excluded, for example, in one embodiment the touchscreen 8 may be include analog keyboards or other known types of interface.

The present invention also provides a monitoring system comprising at least one mobile monitoring device as described above.

The system can usefully include:
one or more devices 1 as described above;
a plurality of reference units installed in the area to be monitored, having known position in a predefined reference system and configured to communicate with said central unit.

The reference units can usefully be marked points, for example marked with radio signals, or with RFID systems or GPS systems, configured to communicate with the central unit through the detection sensors via radio frequency transceivers, or the means of navigation, or the interface unit.

The reference units may be configured to build a localized reference system for the device(s) 1, making navigation more precise and suitable for the particularities of the area to be monitored.

Usefully, the system can include one or more recharging stations operationally communicating with the central unit, where each device 1 can supply energy. In this way, the device 1 can go to the charging station autonomously and the charging can be carried out independently, without the intervention of a manual operator. When the quantity of energy of the device 1 falls below a predefined level, the central unit directs the mobile structure 2 towards the charging station, positioning it in a suitable way to carry out the coupling between the charging unit 12 and the station itself.

Advantageously, the system can comprise at least one sanitization station configured to sanitize and/or sterilize each device 1 and operationally communicate with the central unit of each device 1.

The sanitization and sterilization operation may be required to prevent device 1 from becoming a source of contamination.

Similarly to what is described above, the central unit can direct device 1 near the station and communicate with the latter to initiate operations of sanitization and sterilization in full autonomy, without the intervention of operators.

Example 1—System for Monitoring Controlled Contamination Areas

Figure 2:
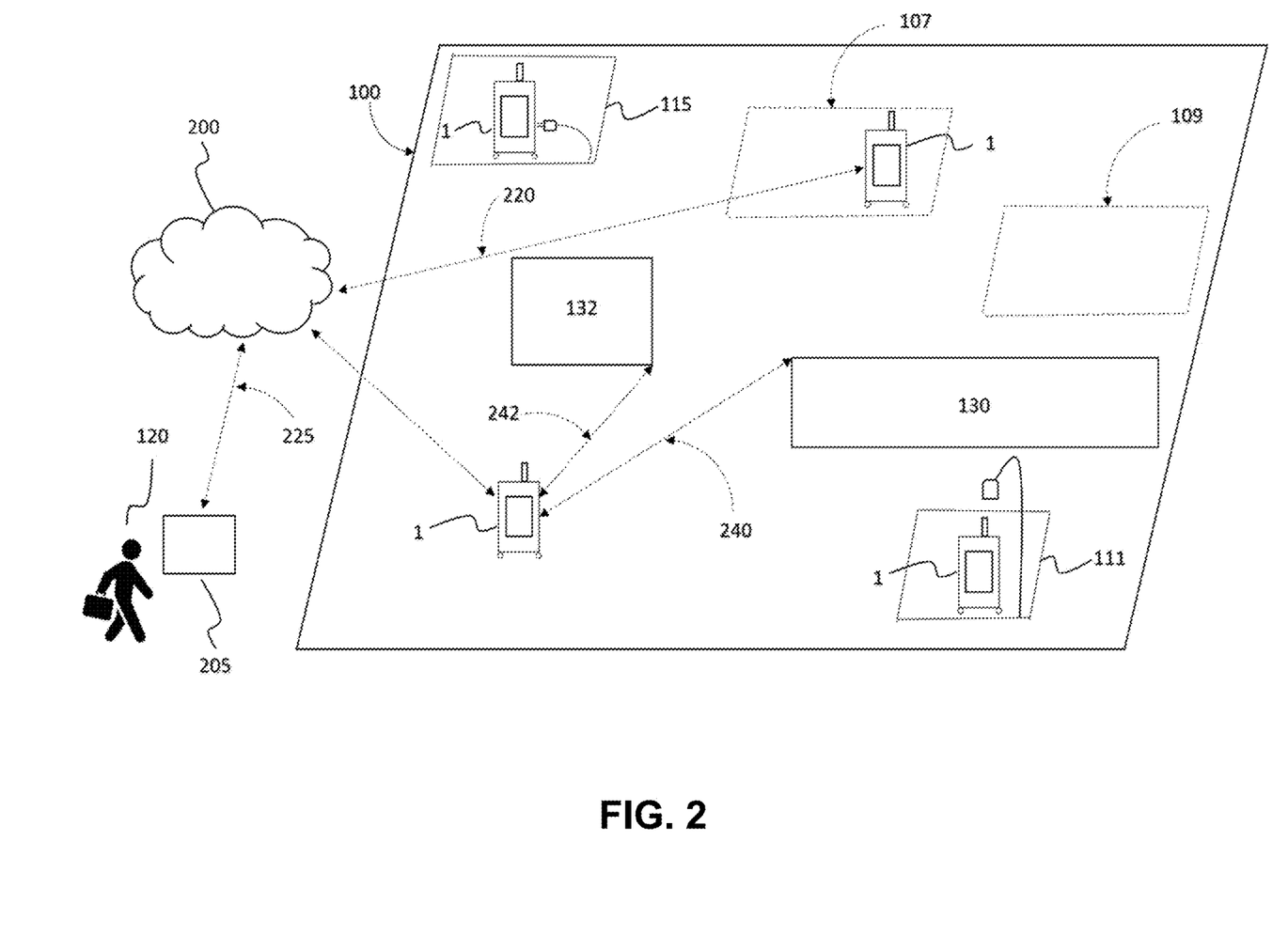
FIG. 2 shows a schematic view of a first embodiment of a system employing multiple devices according to the present invention.

Turning now to FIG. 2, one embodiment of a system for monitoring controlled contamination areas is shown. The system includes several mobile monitoring devices 1, a data network 200, and at least one peripheral external device 205. As shown in FIG. 2, the mobile devices 1 can autonomously move about the area to be monitored 100. The area to be monitored includes predefined points 107, 109. A mobile device 1 may navigate to one of the predefined points 107, 109 in response to instructions received from the data network 200 or based on an onboard set of instructions. Upon reaching one of the predefined starting points 107, 109, the sampling unit of the device may be selectively activated by its central unit to begin sampling operations. Once the sampling operations are complete, the mobile device may move the next predefined point.

The area to be monitored may include one or more obstacles 130, 132. The navigation unit of the mobile device 1 may detect the presence of obstacles 130, 132 via the navigation sensors. In this way the central unit can receive information on the presence of obstacles 130, 132 and, in response, modify the path of the mobile device to avoid them.

The mobile devices of the system may be controlled and/or monitored from a location outside the area to be monitored by an operator 120 via data network 200 and one or more external peripheral devices 205. Useful peripheral devices include smartphones and tablets, or fixed electronic devices, such as PCs or control stations. Thus, each mobile device may be controlled, queried, and/or monitored remotely by the operator 120. Additionally the movements and actions of each mobile device of the system may be coordinated.

The system of FIG. 2 may include a mobile device recharging station 115. When the power supply of the device 1 falls below a predefined level, the central unit may direct the mobile device to the charging station 115. The mobile device may automatically position itself on the charging station to initiate coupling between the charging unit 12 of the device and the charging station 115.

The system of FIG. 2 may include a mobile device sterilization station 111. At certain intervals, and based upon instructions received from the data network 200 or based on an onboard set of instructions, the mobile device may navigate to the sterilization station 111 to be sterilized. The mobile device may automatically position itself on the sterilization station 111 and initiate a sterilization procedure.

Example 2—Reference Units Deployed in the Controlled Contamination Area

Figure 3:
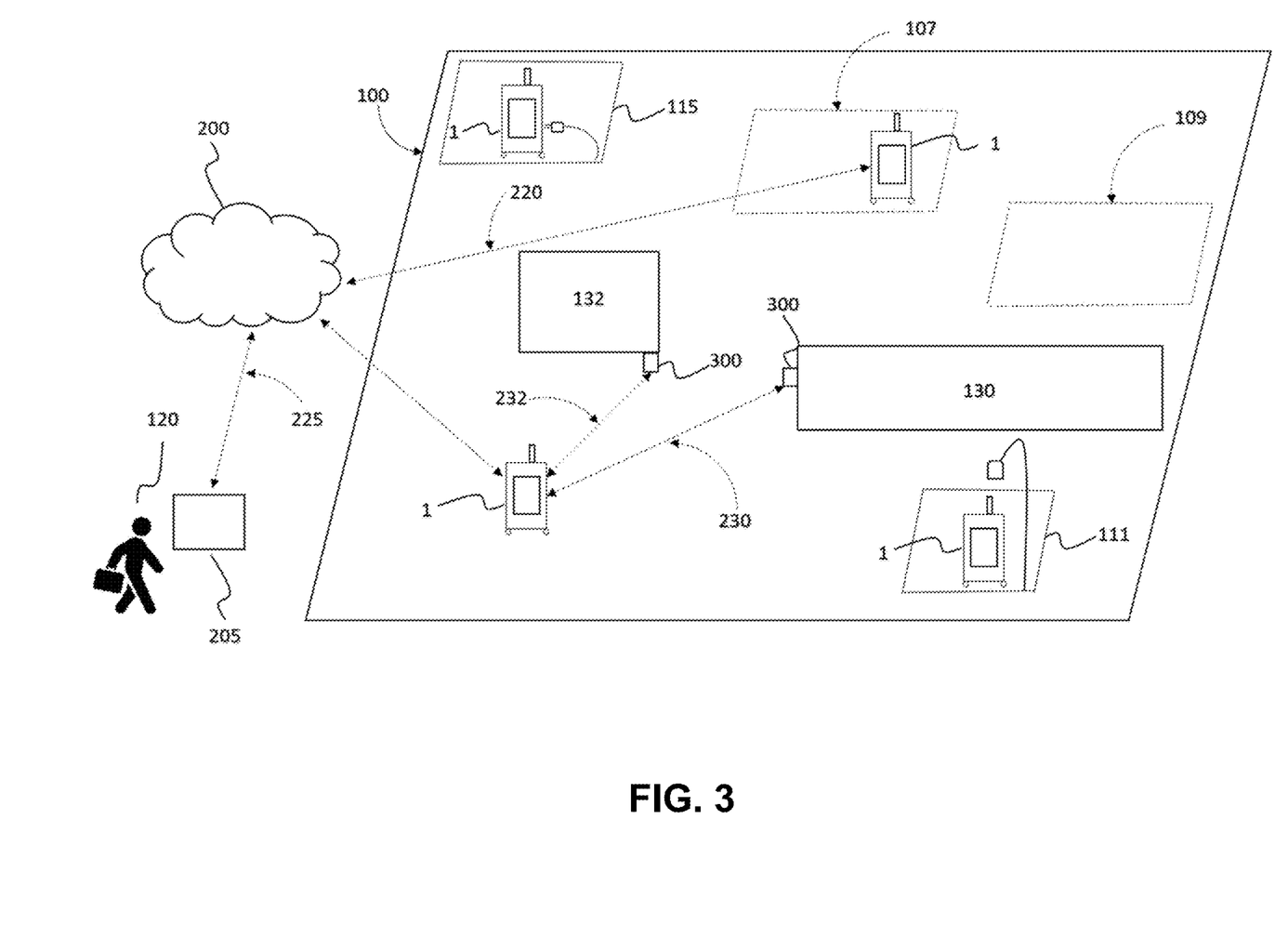
FIG. 3 shows a schematic view of a second embodiment of a system employing multiple devices according to the present invention.

Turning now to FIG. 3, a second embodiment of a system for monitoring controlled contamination areas is shown. The system of FIG. 3 includes the features discussed with respect to FIG. 2, and additionally includes a plurality of reference units 300. The reference units 300 are installed in the area to be monitored 100. Each reference unit 300 has a known position in a predefined reference system. Each reference unit 300 is also configured to communicate with the mobile device.

The reference units 300 may can usefully be marked points, such as locations of obstacles 130, 132. The reference units may also be used to mark predefined sampling points 107, 109, charging station 115, and/or sterilization station 111.

The reference units 300 may employ radio signals, RFID systems and/or GPS systems. The reference units 300 may be configured to communicate with the mobile device via radio frequency transceivers, the navigation unit and/or the interface unit.

The reference units 300 may be configured to build a localized reference system for the device(s) 1, making navigation more precise and suitable for the particularities of the area to be monitored.

Example 3—Mobile Device Schematic

Figure 4:
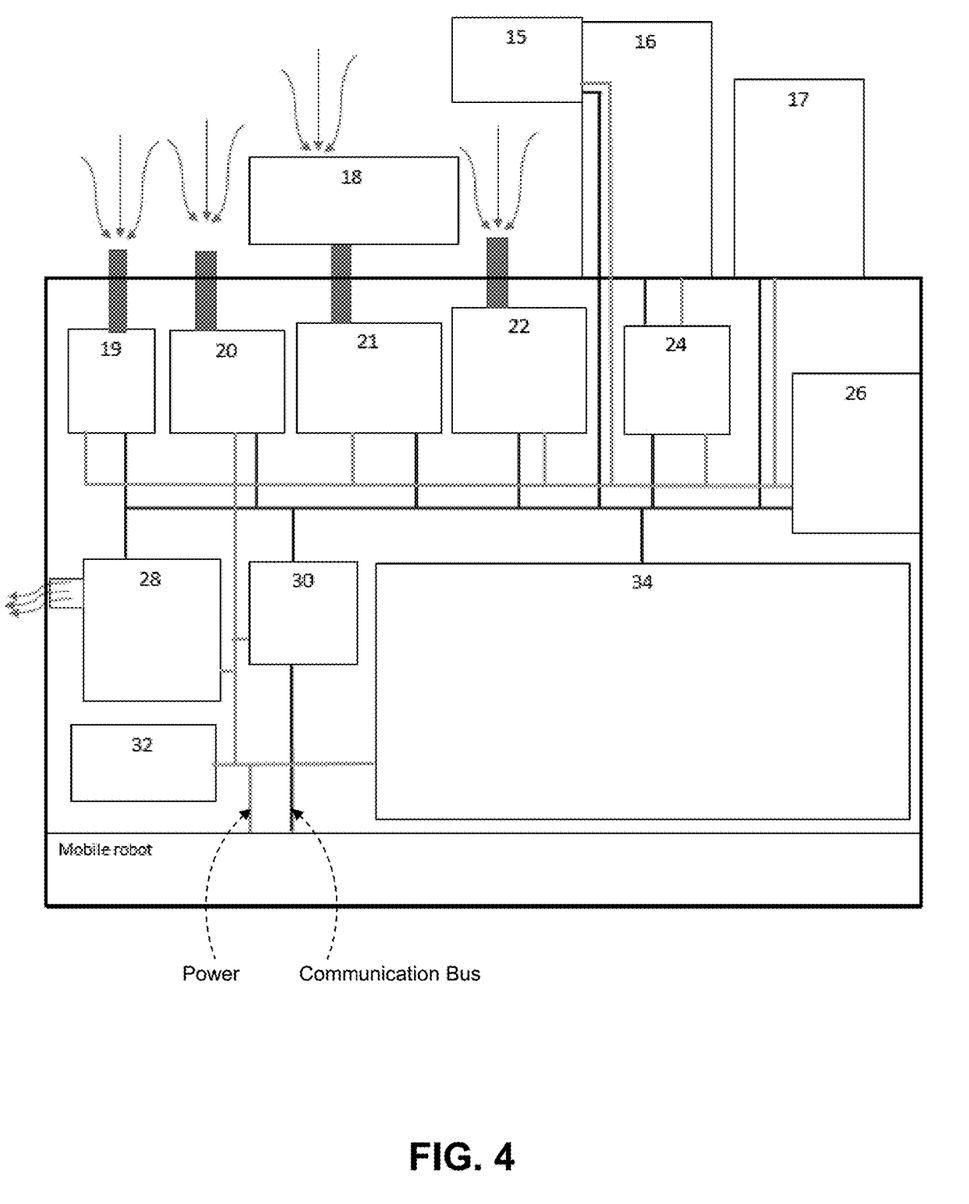
FIG. 4 shows a schematic view of one embodiment of the mobile monitoring device is illustrated.

Turning now to FIG. 4, a schematic view of one embodiment of the mobile monitoring device is illustrated. The illustrated embodiment includes a robotic arm 16. The robotic arm may support a sensing device such 15. In one example the sensing device is a bar code reader. The bar code reader may be configured to read a bar code to associate sampling data with a location within a clean room. Additionally or alternatively, the bar code reader may be configured to read bar codes located on consumable items such as impactors. Additionally or alternatively, the sensing device may include a camera. The camera may be configured to record images for later investigation and for remote real-time viewing of operations within the cleanroom.

The illustrated mobile monitoring device includes a particle counter 19. Particle counter 19 is an instrument able to detect particles in an air flow using laser scattering. Particle counter 19 may include a built in blower to direct the flow of air through the laser.

The illustrated mobile device includes a real-time viable particle counter 20. Real-time viable particle counter 20 is an instrument configured to detect viable biological particles. In one example, real-time viable particle counter 20 employs fluorescence. Additionally or alternatively, the real-time viable particle counter 20 employs chirality to detect viable particles.

The illustrated mobile monitoring device includes a microbiological air sampler 21. The microbiological air sampler 21 comprises a blower configured to collect a stream of air and direct the stream through impactor 18. In one embodiment, the impactor is a single use device configured to trap viable particles for later culturing. In one embodiment, the robotic arm 16 grabs a new impactor 18 and places over the inlet of the microbiological air sampler 21. Next, the robotic arm removes a cap from the impactor 18, exposing a collection surface and sampling begins. Once sampling is complete, the robotic arm 16 replaces the cap onto the impactor 18 to recover the sampling surface. The robotic arm 16 may then place the impactor 18 onto holder 17, where it is ready to be carried by the mobile device to a laboratory to culture the sample.

In one embodiment, impactor 18 includes a petri dish. Thus, the robotic arm 16 may remove a cover on the impactor 18 and place a petri dish in the impactor 18. The robotic arm 16 may then open a cap on the petri dish. Next, the robotic arm 16 may replace the cover on the impactor 18 and sampling may begin. After sampling is complete, the robotic arm 16 may again remove the impactor cover, and replace the cap on the petri dish. The robotic arm 16 may then place the petri dish into the holder 17 where it is ready to be carried by the mobile device to a laboratory for culturing.

In one embodiment, the robotic arm 16 may engage a rodac place located in holder 17. The robotic arm 16 may uncap the rodac plate. The robotic arm 16 may then contact the rodac plate with a surface to be sampled. The robotic arm may replace the cap to the rodac plate and put it back in holder 17 to be transported to a laboratory.

In one embodiment, the robotic arm 16 may engage an impinger, connect the impinger to the inlet of the microbiological air sampler 21, and begin sampling. After sampling is complete, the robotic arm may put the impinger into the holder 17 for transportation to the lab.

The illustrated mobile monitoring device includes a photometer 22. Photometer 22 is an instrument configured to direct particles through a filter via a blower, and scan the surface of the filter.

The illustrated mobile monitoring device includes a robotic arm controller 24. The robotic arm controller 24 is an electronic unit to drive the robotic arm.

The illustrated mobile monitoring device includes an antenna 26. The antenna 26 is configured to connect the mobile device to a data network.

The illustrated mobile monitoring device includes a sanitizer 28. The sanitizer 28 is a device able to sanitize environmental around the mobile station. In one embodiment, the sanitizer 28 employs VHP and/or ozone and/or an ion generator The illustrated mobile monitoring device includes a navigation system 30. The navigation system is functions to guide the mobile monitoring device throughout the cleanroom.

The illustrated mobile monitoring device includes a rechargeable battery 32. The rechargeable battery functions to power the entire mobile system. It can be charged at recharging station.

The illustrated mobile monitoring device includes a panel PC 34. The panel PC 34 includes the following functions:
  Receiving sampling data from the instruments of the mobile monitoring device;
  Downloading recipes to the mobile monitoring device instruments including sampling parameters (e.g., timing, volume of sampling, warning, alarm set up, etc.);
  Starting and stopping sampling at each instrument with the recipe linked to the reached location;

Human Interface on the display including:
   a map of the room to monitor;
   warning, alarm signaling;
   display of recipe and review;
   actions to do in the location;
   status of the actions to do in the location;
   reports of the sampling data that can be filtered by location; group of locations; instruments; mobile station; recipes; and/or set of recipes.
Connection with external data network via wireless connection (e.g., wi-fi; Bluetooth; NFC):
   to upload sampling data to external system;
   to download recipes, and parameters for sampling from external system;
   to check location of the mobile monitoring device (e.g., with a NFC tag or similar);
   to read a tag on consumable item to use for sampling;

Example 4—Sampling Recipe

In some embodiments, the mobile monitoring device may employ recipe-based sampling based on predetermined locations within the area to be monitored. The following is one example of a recipe for sampling:
   Recognize location (by navigation system or with a NFC tag on the wall), e.g., number: location 3
   Start sampling for particle counter for location 3:
      Move the robotic arm and insert the consumable into the inlet of microbiological air sampling;
      Read serial number of the consumable via bar code reader;
      Start sampling of microbiological air sampler;

The present invention has been described up to now with reference to preferred embodiments. It is to be understood that other embodiments may exist which pertain to the same inventive nucleus, as defined by the scope of the claims set out below.

We claim:

1. A mobile monitoring device for monitoring controlled contamination areas, comprising:
   a motorized mobile structure configured to move within a cleanroom;
   a sampling unit positioned on said motorized mobile structure, configured to perform sampling operations of air and/or surfaces of said cleanroom and obtain sampling data;
   a central management and control unit operatively connected to said motorized mobile structure and to said sampling unit;
      wherein said motorized mobile structure is controlled by said central management and control unit to reach predefined points of said area; and
      wherein said sampling unit is selectively activated and/or deactivated by said central management and control unit in correspondence with said predefined points of said area;
   a transceiver operatively connected to said central management and control unit and configured to put said central management and control unit in communication with one or more external peripheral devices, wherein said one or more external peripheral devices are located outside the cleanroom; and
   at least one robotic arm installed on said mobile structure, configured to interact with at least one sampling element usable in said sampling operations.

2. The device of claim 1, comprising at least one memory unit operatively connected to at least one of said central management and control unit and said sampling unit, configured to store said sampling data.

3. The device of claim 1, comprising a navigation unit connected to said central management and control unit, said navigation unit configured to transmit position data to said central management and control unit with respect to which said device is guided in said predefined points.

4. The device of claim 1, wherein said navigation unit comprises at least one location unit configured to emit and/or receive position data comprising location information.

5. The device of claim 4, wherein said navigation unit comprises one or more navigation sensors located on said mobile structure and operatively connected to at least one of said central management and control unit and said location unit, said navigation sensors being configured to detect position data including proximity information.

6. The device of claim 1, comprising at least one radiofrequency detection sensor operatively connected to said central management and control unit and configured to detect coded information and/or recordable data.

7. The device of claim 1, comprising at least one digital camera configured for the acquisition of images and video, operatively connected to said central management and control unit.

8. The device of claim 1, comprising at least one interface unit operatively connected to at least said central management and control unit and configured for interaction with a user.

9. A monitoring system for monitoring controlled contamination areas comprising:
   at least one mobile monitoring device comprising:
      a motorized mobile structure configured to move within a cleanroom;
      a sampling unit positioned on said motorized mobile structure, configured to perform sampling operations of air and/or surfaces of said area and obtain sampling data;
      a central management and control unit operatively connected to said mobile structure and to said sampling unit;
         wherein said motorized mobile structure is controlled by said central management and control unit to reach predefined points of said area;
         wherein said sampling unit is selectively activated and/or deactivated by said central management and control unit in correspondence with said predefined starting points of said sampling operations;
   a data network in operational communication with the at least one mobile monitoring device;
   an external peripheral device operationally connected to the data network, wherein the external peripheral device is located outside the cleanroom; and
   at least one sanitizing station operatively communicating with said device and configured to sanitize and/or sterilize the device.

10. The system of claim 9 comprising a plurality of reference units installed in the area to be monitored, each reference unit having a known position in a predefined reference system and configured to communicate with said device.

11. The system of claim 10 wherein the reference units comprise RFID systems.

12. The system of claim 10 wherein the reference units comprise GPS systems.

13. The system of claim 10, wherein the reference units are configured to communicate with the central management and control unit through the detection sensors via radio frequency transceivers.

14. The system of claim 10, wherein the reference units are configured to communicate with the central management and control unit via a digital camera of the device.

15. The system of claim 9 comprising at least one charging station operatively communicating with said device.

16. The system of claim 15, wherein the device is configured such that when the quantity of energy of the device falls below a predefined level, the central management and control unit directs the mobile structure to the charging station and couples the device to the charging station.

17. The system of claim 9, wherein the device is configured to navigate to predefined points of the area to be monitored and selectively activate the sampling unit at the predefined points.

18. The system of claim 9, wherein the device is configured to distinguish between viable particle and non-viable particles.

19. The system of claim 18, wherein the device includes a particle counter and a real-time viable particle counter.

20. The system of claim 9, wherein the central management and control unit is configured to direct the device to navigate to the sanitizing station.

21. The system of claim 20, wherein the device is configured to direct the sanitizing station to sanitize the surfaces of the device.

22. The system of claim 9, wherein the mobile device is configured to automatically position itself on the sterilization station and initiate a sterilization procedure.

* * * * *

UNITED STATES PATENT AND TRADEMARK OFFICE
CERTIFICATE OF CORRECTION

| | | |
|---|---|---|
| PATENT NO. | : 11,540,248 B2 | Page 1 of 1 |
| APPLICATION NO. | : 17/087906 | |
| DATED | : December 27, 2022 | |
| INVENTOR(S) | : Giovanni Scialò et al. | |

It is certified that error appears in the above-identified patent and that said Letters Patent is hereby corrected as shown below:

On the Title Page (73) Assignee:
PARTICLE MEASURING SYSTEMS, INC., Boulder, CO (US)

Should read:
PARTICLE MEASURING SYSTEMS, INC., Boulder, CO (US);
PHARMA INTEGRATION S.R.L., Siena (IT).

Signed and Sealed this
Sixteenth Day of September, 2025

Coke Morgan Stewart
*Acting Director of the United States Patent and Trademark Office*